(12) United States Patent
Prencipe et al.

(10) Patent No.: US 9,789,048 B2
(45) Date of Patent: *Oct. 17, 2017

(54) ORAL CARE COMPOSITIONS AND METHODS

(71) Applicant: COLGATE-PALMOLIVE COMPANY, New York, NY (US)

(72) Inventors: Michael Prencipe, West Windsor, NJ (US); Suzanne Jogun, Wayne, NJ (US); Betty Won, New Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/106,507

(22) PCT Filed: Dec. 20, 2013

(86) PCT No.: PCT/US2013/076896
§ 371 (c)(1),
(2) Date: Jun. 20, 2016

(87) PCT Pub. No.: WO2015/094337
PCT Pub. Date: Jun. 25, 2015

(65) Prior Publication Data
US 2016/0331669 A1    Nov. 17, 2016

(51) Int. Cl.
| | | |
|---|---|---|
| *A61K 8/81* | (2006.01) |
| *A61Q 11/00* | (2006.01) |
| *A61K 8/19* | (2006.01) |
| *C09D 143/02* | (2006.01) |
| *A61K 8/20* | (2006.01) |
| *A61K 8/34* | (2006.01) |
| *A61K 8/43* | (2006.01) |
| *A61K 8/49* | (2006.01) |
| *A61K 8/58* | (2006.01) |

(52) U.S. Cl.
CPC .............. *A61K 8/8152* (2013.01); *A61K 8/19* (2013.01); *A61K 8/20* (2013.01); *A61K 8/347* (2013.01); *A61K 8/43* (2013.01); *A61K 8/4926* (2013.01); *A61K 8/58* (2013.01); *A61Q 11/00* (2013.01); *C09D 143/02* (2013.01); *A61K 2800/28* (2013.01); *A61K 2800/43* (2013.01); *A61K 2800/48* (2013.01); *A61K 2800/524* (2013.01); *A61K 2800/5424* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 2004/0208834 | A1* | 10/2004 | Koudate | A61K 8/8135 424/49 |
| 2009/0136432 | A1* | 5/2009 | Strand | A61K 8/19 424/52 |
| 2011/0089073 | A1 | 4/2011 | Baig et al. | |

FOREIGN PATENT DOCUMENTS

| | | | | |
|---|---|---|---|---|
| WO | WO 2008/041055 | * | 4/2008 | A61K 8/19 |

OTHER PUBLICATIONS

International Search Report for International Application No. PCT/US2013/076896 mailed Nov. 11, 2014, 3 pages.
SIPOMER® PAM-4000, Product Data Sheet n002195, Solvay Rhodia, 2012, (http://www.rhodia.com/product-literature-download.action?docId=0901663680d8e32e&docLanguage=EN&docType=TDS&output=BINARY& productName=Sipomer+PAM-4000).

* cited by examiner

*Primary Examiner* — Brian Gulledge

(57) ABSTRACT

Provided is an oral care composition comprising a phosphate/acrylate co-polymer, a tin salt, and an orally acceptable carrier, and methods of using the same.

16 Claims, No Drawings

ORAL CARE COMPOSITIONS AND METHODS

BACKGROUND

Many individuals desire a "bright" smile and white teeth, and consider dull and stained teeth cosmetically unattractive. Unfortunately, without preventive or remedial measures, stained teeth are almost inevitable due to the absorbent nature of dental material. Everyday activities such as smoking or other oral use of tobacco products, and eating, chewing or drinking certain foods and beverages (in particular coffee, tea, coke, and red wine), cause undesirable staining of surfaces of teeth. Staining can also result from microbial activity, including that associated with dental plaque. The chromogens or color causing substances in these materials become part of the pellicle layer and can permeate the enamel layer. Even with regular brushing and flossing, years of chromogen accumulation can impart noticeable tooth discoloration.

A tooth is comprised of an inner dentin layer and an outer hard enamel layer that is the protective layer of the tooth. The enamel layer of a tooth is naturally opaque, and white or a slightly off-white color. The enamel layer is composed of hydroxyapatite mineral crystals that create a somewhat porous surface. These hydroxyapatite crystals form microscopic hexagonal rods or prisms that make up the enamel surface. As a result, the surface of the enamel presents microscopic spaces or pores between the prisms. Without limiting the mechanism, function or utility of present invention, it is believed that this porous nature of the enamel is where discoloring substances permeate the enamel and discolor the teeth.

To combat staining and brighten or restore the natural enamel color, products containing bleaching materials are commercially available for professional and consumer use. The most commonly accepted chemicals used in teeth whitening today are peroxides. Peroxides are generally deemed safe from a physiological standpoint, and can be effective to whiten teeth. Such peroxides include hydrogen peroxide, carbamide peroxide, sodium perborate, and sodium percarbonate. When these peroxides are in appropriate contact with teeth they will usually oxidize stains, rendering the teeth whiter.

Professional dental treatments frequently include a tooth surface preparation such as acid etching followed by the application of highly concentrated bleaching solutions (e.g. up to 37% hydrogen peroxide) and/or the application of heat or light. These procedures provide rapid results, but are expensive, and often require several trips to the dentist. In many cases, the patient's lips are uncomfortably retracted during the entire treatment and the patient is confined to sitting in the dental chair.

Alternatively, at home bleaching systems can be used. These systems have gained significant popularity in the past decade because of reduced cost, and increased convenience.

Current home treatment methods include abrasive toothpastes, toothpastes that produce oxides, whitening gels for use with a dental tray, and whitening strips. The effectiveness of such techniques depends on a variety of factors including the type and intensity of the stain, the type of bleaching agent, contact time of the bleaching agent on the teeth, the amount of available bleaching active in the composition, the ability of the bleaching agent to penetrate the tooth enamel, and consumer compliance. Effectiveness is also dependent on the amount of bleaching active in the composition, the ability of the active to be released during use, and the stability of the active in the product. However, the effectiveness of many of these treatments is adversely affected because of deficiencies in one or more factors relating to the composition and consumer compliance.

Biofilms form when bacteria adhere to surfaces in some form of watery environment and begin to excrete a slimy, glue-like substance that can stick to all kinds of materials—metals, plastics, soil particles, medical implant materials, biological tissues. Biofilms can be formed by a single bacterial species, but biofilms more often consist of many species of bacteria, as well as fungi, algae, protozoa, debris, and corrosion products. Essentially, a biofilm may form on any surface exposed to bacteria and some amount of water. Dental plaque is a yellowish biofilm that builds up on the teeth. Biofilms contain communities of disease-causing bacteria and their uncontrolled accumulation has been associated with cavities and gum disease (both gingivitis and periodontitis).

There is thus a need for novel oral compositions and methods that may inhibit staining and/or biofilm formation.

BRIEF SUMMARY

Provided is an oral care composition comprising a phosphate/acrylate co-polymer, a tin salt and an orally acceptable carrier, and methods of using the same.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein, an "oral care composition" refers to a composition for which the intended use can include oral care, oral hygiene, or oral appearance, or for which the intended method of use can comprise administration to the oral cavity. In some embodiments, an oral care composition is not intentionally swallowed, but is rather retained in the oral cavity for a time sufficient to effect the intended utility. The oral care compositions as disclosed herein may be used in nonhuman mammals such as companion animals (e.g., dogs and cats), as well as by humans. In some embodiments, the oral care compositions as disclosed herein are used by humans.

As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers include, for example, one or more of the following: water, a thickener, a buffer, a humectant, a surfactant, an abrasive, a sweetener, a flavorant, a visual aid (e.g., a pigment, a dye, or a mixture thereof), an anti-caries agent, an anti-bacterial, a whitening agent, a desensitizing agent, a vitamin, a preservative, an enzyme, and mixtures thereof.

As used herein, a "tartar control agent" refers to a compound or a mixture of compounds that inhibit the formation of tartar, a mixture of calcium phosphates on organic matrices, and/or the deposition of plaque on teeth to form tartar (calculus).

As used herein, "chemical stain" refers to a discoloration of a dental surface caused by adsorption or absorption of a colored agent on or into the surface, or caused by chemical reaction of material of the dental surface (e.g., dental enamel) with a colored or noncolored agent contacting the surface. "Chemical staining" herein means formation and/or development of a chemical stain.

As used herein, "dental surface" refers to a surface of a natural tooth or a hard surface of artificial dentition including a denture, dental plate, crown, cap, filling, bridge, dental implant and the like. In some embodiments, the dental surface is a natural tooth.

Biofilm comprises a diverse microbial community on the tooth surface embedded in a matrix of polymers of bacterial and salivary origin. Once a tooth surface is cleaned, a conditioning film of proteins and glycoproteins may be adsorbed rapidly to the tooth surface. Biofilm formation involves the interaction between early bacterial colonisers and this film. Subsequently, secondary colonisers adhere to the already attached early colonisers (co-aggregation) and this process contributes to the development of a matured biofilm. Inhibiting the growth of biofilm may involve preventing and minimizing the re-attachment of bacteria onto the tooth surfaces.

The phosphate side group of a phosphate/acrylate co-polymer, as disclosed herein, may function as an anchor to deposit the co-polymer onto the tooth surface thereby forming a physical layer on the tooth surface that may inhibit staining and/or biofilm formation. Without being bound by theory, the co-polymer may act by forming a barrier on the tooth surface ultimately lowering the surface energy for bacterial attachment. The co-polymer may also prevent bacteria from sticking together.

As used herein, "phosphate/acrylate co-polymer" refers to a polymer made up of acrylate monomers and phosphate-bearing monomers, e.g., a co-polymerized product of a mixture of acrylic acid, methacrylic acid, and 2-hydroxyethyl methacrylate phosphates of Formula 1:

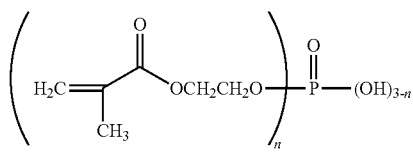

wherein n is 0, 1 or 2. In some embodiments, the phosphate/acrylate co-polymer is a co-polymerized product of a mixture of acrylic acid, methacrylic acid, and 2-hydroxyethyl methacrylate phosphates of Formula 1, comprising acrylic acid in a molar percentage of 70-90%, 80-90%, or about 85%; methacrylic acid in a molar percentage of 5-20%, 5-15%, or about 11%, and hydroxyethyl methacrylate phosphates of Formula 1 in a molar percentage of 1-10%, 2-6%, or about 4%. In some embodiments, the phosphate/acrylate co-polymer has a weight average molecular weight of from 10 to 500 kDa, optionally, 10 to 200 kDa, 10 to 40 kDa, 15 to 25, or 17 to 23 kDa, and the phosphate/acrylate co-polymer is below its glass transition temperature. In certain embodiments, the weight average molecular weight is 10 to 40 kDa. In other embodiments, the weight average molecular weight is 17 to 23 kDa. For example, in a particular embodiment, the phosphate/acrylate copolymer is a random copolymer that is the copolymerized product of a mixture of, in the relative amounts set forth in Table 1 below, 2-hydroxyethy methacrylate phosphates, acrylic acid, and methacrylic acid.

TABLE 1

| Monomer Name and Structure | Monomer Weight Ratio (weight %) | Monomer Molar Ratio (Mole %) |
|---|---|---|
| 2-hydroxyethyl methacylate phosphates<br><br>$\left( H_2C=\underset{CH_3}{C}-\underset{\parallel}{\overset{O}{C}}-OCH_2CH_2O \right)_n \overset{O}{\underset{\parallel}{P}}-(OH)_{3-n}$<br><br>mixture of n = 0, n = 1, and n = 2 | 11 | 4 |
| acrylic acid<br><br>$H_2C=\underset{H}{C}-\underset{\parallel}{\overset{O}{C}}-OH$ | 75 | 85 |

TABLE 1-continued

| Monomer Name and Structure | Monomer Weight Ratio (weight %) | Monomer Molar Ratio (Mole %) |
|---|---|---|
| methacrylic acid | 14 | 11 |

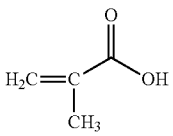

Phosphate/acrylate co-polymers as described include DV8801 (Rhodia).

Provided herein is an oral care composition (Composition 1) comprising a phosphate/acrylate co-polymer, a tin salt, and an orally acceptable carrier. For example, further provided herein is Composition 1 as follows:

1.1 Composition 1 wherein the composition comprises 0.1 to 10 weight % phosphate/acrylate co-polymer, e.g., 0.2 to 9 weight % phosphate/acrylate co-polymer, e.g., 0.3 to 8 weight % phosphate/acrylate co-polymer, e.g., 0.4 to 7 weight % phosphate/acrylate co-polymer, e.g., 0.5 to 6 weight % phosphate/acrylate co-polymer, e.g., 0.5 to 5 weight % phosphate/acrylate co-polymer, e.g., 0.5 to 4 weight % phosphate/acrylate co-polymer, e.g., 0.5 to 3 weight % phosphate/acrylate co-polymer, e.g., 0.5 to 2 weight % phosphate/acrylate co-polymer, e.g., 1 to 10 weight % phosphate/acrylate co-polymer, e.g., 1 to 8 weight % phosphate/acrylate co-polymer, e.g., 1 to 6 weight % phosphate/acrylate co-polymer, e.g., 1 to 5 weight % phosphate/acrylate co-polymer, e.g., 1 to 4 weight % phosphate/acrylate co-polymer, e.g., 1 to 3 weight % phosphate/acrylate co-polymer, e.g., 1 to 2 weight % phosphate/acrylate co-polymer.

1.2 Composition 1 or 1.1 wherein the tin salt is an orally acceptable stannous (Sn(II)) salt, e.g., a stannous halide, e.g., selected from stannous chloride, stannous fluoride and mixtures thereof.

1.3 Composition 1, 1.1, or 1.2 wherein the composition comprises $SnCl_2$.

1.4 Composition 1 or 1.1-1.3 wherein the composition comprises 0.1 to 10 weight % $SnCl_2$, e.g., 0.1 to 5 weight % $SnCl_2$, e.g., 0.1 to 3 weight % $SnCl_2$, e.g., 0.1 to 1.5 weight % $SnCl_2$, e.g., 0.5 to 1.2 weight % $SnCl_2$.

1.5 Composition 1 or 1.1-1.4 wherein the composition comprises water, a thickener, a buffer, a humectant, a surfactant, an abrasive, a sweetener, a flavorant, a visual aid (e.g., a pigment, a dye, or a mixture thereof), an anti-caries agent, an anti-bacterial, a whitening agent, a desensitizing agent, a preservative, or a mixture thereof.

1.6 Composition 1 or 1.1-1.5 wherein the composition comprises water.

1.7 Composition 1 or 1.1-1.6 wherein the composition comprises a thickener.

1.8 Composition 1.7 wherein the thickener is a mixture of thickening silica and carrageenan gum.

1.9 Composition 1 or 1.1-1.8 wherein the composition comprises a buffer.

1.10 Composition 1.9 wherein the buffer is sodium hydroxide.

1.11 Composition 1 or 1.1-1.10 wherein the composition comprises a humectant.

1.12 Composition 1.11 wherein the humectant is a mixture of glycerin, sorbitol, and propylene glycol.

1.13 Composition 1 or 1.1-1.12 wherein the composition comprises a surfactant.

1.14 Composition 1.13 wherein the surfactant is sodium lauryl sulfate.

1.15 Composition 1 or 1.1-1.14 wherein the composition comprises an abrasive.

1.16 Composition 1.15 wherein the abrasive comprises silica.

1.17 Composition 1 or 1.1-1.16 wherein the composition comprises a sweetener.

1.18 Composition 1.17 wherein the sweetener is sodium saccharin.

1.19 Composition 1 or 1.1-1.18 wherein the composition comprises a flavorant.

1.20 Composition 1 or 1.1-1.19 wherein the composition comprises a visual aid.

1.21 Composition 1.20 wherein the visual aid is titanium dioxide.

1.22 Composition 1 or 1.1-1.21 wherein the composition comprises an anti-caries agent.

1.23 Composition 1.22 wherein the anti-caries agent is a fluoride ion source.

1.24 Composition 1.23 wherein the fluoride ion source is stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, or a mixture thereof.

1.25 Composition 1.24 wherein the anticaries agent is sodium fluoride.

1.26 Composition 1 or 1.1-1.25 wherein the anti-bacterial agent is triclosan, cetylpyridinium chloride (CPC), chlorhexidine (CHX), stannous salts, essential oils, water soluble zinc salts, water insoluble zinc salts, e.g., ZnO or zinc citrate, or a mixture thereof e.g., wherein the anti-bacterial agent is triclosan, e.g., wherein the anti-bacterial agent is ZnO, e.g., wherein the anti-bacterial agent is zinc citrate, e.g., wherein the anti-bacterial agent is a mixture thereof.

1.27 Composition 1 or 1.1-1.27 wherein the composition comprises an anti-attachment agent selected from Solbrol, Decapinol, chitosan, or a mixture thereof, e.g., wherein the composition comprises Solbrol, e.g., wherein the composition comprises Decapinol, e.g., wherein the composition comprises chitosan, e.g., wherein the composition comprises a mixture thereof.

1.28 Composition 1 or 1.1-1.28 wherein the composition comprises a whitening agent.

1.29 Composition 1.29 wherein the whitening agent is hydrogen peroxide.

1.30 Composition 1.30 wherein the composition comprises a polymer-peroxide complex, e.g., a cross-linked poly(vinyl)pyrrolidone hydrogen peroxide complex.
1.31 Composition 1 or 1.1-1.31 wherein the composition comprises a desensitizing agent, a vitamin, a preservative, an enzyme, or a mixture thereof.
1.32 Composition 1 or 1.1-1.32 wherein the composition is a mouthwash, toothpaste, tooth gel, tooth powder, non-abrasive gel, mousse, foam, mouth spray, lozenge, oral tablet, dental implement, or pet care product.
1.33 Composition 1 or 1.1-1.33 wherein the composition is a mouthwash.
1.34 Composition 1 or 1.1-1.34 wherein the composition is a toothpaste.
1.35 Any foregoing compositions wherein the phosphate/acrylate co-polymer is a co-polymerized product of a mixture of acrylic acid, methacrylic acid, and 2-hydroxyethyl methacrylate phosphates of Formula 1:

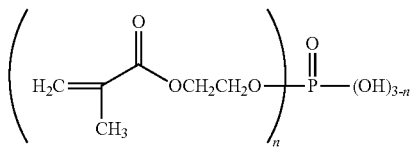

wherein n is 0, 1 or 2.
1.36 Any foregoing compositions wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 80-90%, e.g., about 85%; methacrylic acid in a molar percentage of 5-15%, e.g., about 11%, and hydroxyethyl methacrylate phosphates of Formula 1 in a molar percentage of 2-6%, e.g., about 4%.
1.37 Any foregoing compositions wherein the phosphate/acrylate co-polymer has an average molecular weight of from 10 to 40 kDa, e.g., 20 to 30 kDa.
1.38 Any foregoing compositions wherein the phosphate/acrylate copolymer is a random copolymer having a weight average molecular weight of about 20,000 to 30,000 grams per mole that is the copolymerized product of a mixture of acrylic acid, methacrylic acid, and 2-hydroxyethy methacrylate phosphates of Formula 1, e.g., in a molar ratio of about 85:11:4.

In some embodiments, the oral care compositions disclosed herein, e.g., Composition 1, e.g., 1.1-1.39, comprise water. Water employed in the preparation of the oral care compositions disclosed herein, e.g., Composition 1, e.g., 1.1-1.39, should be deionized and free of organic impurities. Water may make up the balance of the oral care composition. In some embodiments, the oral care compositions disclosed herein, e.g., Composition 1, e.g., 1.1-1.39, comprise 0 to 90 weight % water, e.g., 0.1 to 90 weight % water, e.g., 1 to 80 weight % water, e.g., 2 to 70 weight % water, 5 to 60 weight % water, e.g., 5 to 50 weight % water, e.g., 20 to 60 weight % water, e.g., 10 to 50 weight % water. This amount of water includes the free water which is added plus that amount which is introduced with other components of the oral care composition, such as with sorbitol.

A thickener provides a desirable consistency and/or stabilizes and/or enhances performance (e.g., provides desirable active release characteristics upon use) of the oral care composition. In some embodiments, the oral care compositions disclosed herein, e.g., Composition 1, e.g., 1.1-1.39, comprise from 0.01 to 15 weight % of a thickener, 0.1 to 15 weight % of a thickener, e.g., 0.1 to 10 weight % of a thickener. e.g., 0.1 to 5 weight % of a thickener, e.g., 0.5 to 10 weight % of a thickener, e.g., 0.5 to 5 weight % of a thickener, e.g., 1 to 4 weight % of a thickener, e.g., 2 to 5 weight % of a thickener, e.g., 2 to 4 weight % of a thickener, e.g., 3 to 4 weight % of a thickener. Higher weight percentages may be used for chewing gums, lozenges and breath mints, sachets, non-abrasive gels and subgingival gels. Thickeners that may be used in the oral care compositions disclosed herein, e.g., Composition 1, e.g., 1.1-1.39, include, for example, carboxyvinyl polymers, carrageenan (also known as carrageenan gum), hydroxyethyl cellulose (HEC), natural and synthetic clays (e.g., Veegum and laponite), water soluble salts of cellulose ethers (e.g., sodium carboxymethylcellulose (CMC) and sodium carboxymethyl hydroxyethyl cellulose), natural gums (e.g., gum karaya, xanthan gum, gum arabic, and gum tragacanth), colloidal magnesium aluminum silicate, silica (e.g., finely divided silica), polyvinyl pyrrolidone, carbowaxes, fatty acids and salts thereof, and mixtures thereof. In some embodiments, a mixture of thickening silica and carrageenan gum is used as the thickener in the oral care compositions disclosed herein, e.g., Composition 1. e.g., 1.1-1.39. In some embodiments, the oral care compositions disclosed herein, e.g., Composition 1, e.g., 1.1-1.39, comprise from 0.01 to 15 weight % of thickening silica and carrageenan gum, 0.1 to 15 weight % of thickening silica and carrageenan gum, e.g., 0.1 to 10 weight % of thickening silica and carrageenan gum, e.g., 0.1 to 5 weight % of thickening silica and carrageenan gum, e.g., 0.5 to 10 weight % of thickening silica and carrageenan gum, e.g., 0.5 to 5 weight % of thickening silica and carrageenan gum, e.g., 1 to 4 weight % of thickening silica and carrageenan gum, e.g., 2 to 5 weight % of thickening silica and carrageenan gum. e.g., 2 to 4 weight % of thickening silica and carrageenan gum, e.g., 3 to 4 weight % of thickening silica and carrageenan gum.

A buffer adjusts the pH of oral care compositions, for example, to a range of about pH 4.0 to about pH 6.0. In some embodiments, the oral care compositions disclosed herein, e.g., Composition 1, e.g., 1.1-1.39, comprise from 0.5 to 10 weight % of a buffer, e.g., 0.5 to 5 weight % of a butter, e.g., 0.5 to 4 weight % of a buffer, e.g., 0.5 to 3 weight % of a buffer, e.g., 0.5 to 2 weight % of a buffer, e.g., 1 to 2 weight % of a buffer. Buffers that may be used in the oral care compositions disclosed herein, e.g., Composition 1, e.g., 1.1-1.39, include, for example, sodium bicarbonate, sodium phosphate {e.g., monosodium phosphate ($NaH_2PO_4$), disodium phosphate ($Na_2HPO_4$), trisodium phosphate ($Na_3PO_4$)}, sodium hydroxide, sodium carbonate, sodium acid pyrophosphate, citric acid, sodium citrate, and mixtures thereof. In some embodiments, sodium hydroxide is used as the buffer in the oral care compositions disclosed herein, e.g., Composition 1, e.g., 1.1-1.39. In some embodiments, the oral care compositions disclosed herein, e.g., Composition 1, e.g., 1.1-1.39, comprise from 0.5 to 10 weight % of sodium hydroxide. e.g., 0.5 to 5 weight % of sodium hydroxide, e.g., 0.5 to 4 weight % of sodium hydroxide, e.g., 0.5 to 3 weight % of sodium hydroxide, e.g., 0.5 to 2 weight % of sodium hydroxide, e.g., 1 to 2 weight % of sodium hydroxide.

A humectant keeps oral care compositions from hardening upon exposure to air. Certain humectants can also impart desirable sweetness or flavor to oral care compositions. In some embodiments, the oral care compositions disclosed herein, e.g., Composition 1, e.g., 1.1-1.39, comprise, on a pure humectant basis, from 0 to 70 weight % of a humectant, e.g., from 10 to 70 weight % of a humectant, e.g., from 10 to 65 weight % of a humectant, e.g., from 10 to 60 weight % of a humectant, e.g., from 10 to 50 weight % of a humectant, e.g., from 20 to 50 weight % of at a humectant, e.g., from 30 to 50 weight % of a humectant, e.g., from 40 to 50 weight % of a humectant. Humectants that may be used in the oral care compositions disclosed herein, e.g., Composition 1, e.g., 1.1-1.39, include, for example, glycerin, sorbitol, xylitol, butylene glycol, polyethylene glycol, propylene glycol, trimethyl glycine, and mixtures thereof. In some embodiments, a mixture of glycerin, sorbitol, and propylene glycol is used as the humectant in the oral care compositions disclosed herein, e.g., Composition 1, e.g., 1.1-1.39. In some embodiments, the oral care compositions disclosed herein, e.g., Composition 1. e.g., 1.1-1.39, comprise, on a pure humectant basis, from 0 to 70 weight % of glycerin, sorbitol, and propylene glycol, e.g., from 10 to 70 weight % of glycerin, sorbitol, and propylene glycol, e.g., from 10 to 65 weight % of glycerin, sorbitol, and propylene glycol, e.g., from 10 to 60 weight % of glycerin, sorbitol, and propylene glycol, e.g., from 10 to 50 weight % of glycerin, sorbitol, and propylene glycol, e.g., from 20 to 50 weight % of glycerin, sorbitol, and propylene glycol, e.g., from 30 to 50 weight % of glycerin, sorbitol, and propylene glycol, e.g., from 40 to 50 weight % of glycerin, sorbitol, and propylene glycol.

In some embodiments, the oral care compositions disclosed herein, e.g., Composition 1, e.g., 1.1-1.39, comprise a surfactant, e.g., selected from anionic, cationic, zwitterionic, and nonionic surfactants, and mixtures thereof. In some embodiments, the surfactant is reasonably stable throughout a wide pH range. Surfactants are described in, for example, U.S. Pat. No. 3,959,458, to Agricola et al; U.S. Pat. No. 3,937,807, to Haefele; and U.S. Pat. No. 4,051,234, to Gieske et al., which are incorporated herein by reference in their entirety. In some embodiments, the oral care compositions disclosed herein, e.g., Composition 1, e.g., 1.1-1.39, comprise from 0.01 to 10 weight % of a surfactant, e.g., 0.05 to 5 weight % of a surfactant, e.g., 0.1 to 10 weight % of a surfactant, e.g., 0.1 to 5 weight % of a surfactant, e.g., 0.1 to 2 weight % of a surfactant, e.g., 0.5 to 2 weight % of a surfactant. In some embodiments, the oral care compositions disclosed herein, e.g., Composition 1, e.g., 1.1-1.39, comprise from about 0.01 to 10 weight % of an anionic surfactant, e.g., 0.05 to 5 weight % of an anionic surfactant, e.g., 0.1 to 10 weight % of an anionic surfactant, e.g., 0.1 to 5 weight % of an anionic surfactant, e.g., 0.1 to 2 weight % of an anionic surfactant, e.g., 0.5 to 2 weight % of an anionic surfactant.

Anionic surfactants that may be used in the oral care compositions disclosed herein, e.g., Composition 1, e.g., 1.1-1.39, include, for example,
  i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
  ii. higher alkyl sulfates, such as sodium lauryl sulfate,
  iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate ($CH_3(CH_2)_{10}CH_2(OCH_2CH_2)_2OSO_3Na$),
  iv. higher alkyl aryl sulfonates such as sodium dodecyl benzene sulfonate (sodium lauryl benzene sulfonate), and
  v. higher alkyl sulfoacetates, such as sodium lauryl sulfoacetate (dodecyl sodium sulfoacetate), higher fatty acid esters of 1.2 dihydroxy propane sulfonate, sulfocolaurate (N-2-ethyl laurate potassium sulfoacetamide) and sodium lauryl sarcosinate.

As used herein, "higher alkyl" refers to $C_{6-30}$ alkyl.

In some embodiments, the oral care compositions disclosed herein, e.g., Composition 1, e.g., 1.1-1.39, comprise an anionic surfactant. In some embodiments, the anionic surfactant is the water soluble salt of alkyl sulfates having from 10 to 18 carbon atoms in the alkyl radical and water soluble salts of sulfonated monoglycerides of fatty acids having from 10 to 18 carbon atoms. Sodium lauryl sulfate, sodium lauroyl sarcosinate, and sodium coconut monoglyceride sulfonates are examples of anionic surfactants of that type. In some embodiments, the oral care compositions disclosed herein. e.g., Composition 1, e.g., 1.1-1.39, comprise sodium lauryl sulfate, sodium ether lauryl sulfate, or a mixture thereof. In some embodiments, the oral care compositions disclosed herein, e.g., Composition 1, e.g., 1.1-1.39, comprise sodium lauryl sulfate. In some embodiments, the oral care compositions disclosed herein, e.g., Composition 1, e.g., 1.1-1.39, comprise from 0.01 to 10 weight % sodium lauryl sulfate, e.g., 0.05 to 5 weight % sodium lauryl sulfate, e.g., 0.1 to 10 weight % sodium lauryl sulfate, e.g., 0.1 to 5 weight % o sodium lauryl sulfate, e.g., 0.1 to 2 weight % sodium lauryl sulfate, e.g., 0.5 to 2 weight % sodium lauryl sulfate.

An abrasive removes debris and surface stains. In some embodiments, the oral care compositions disclosed herein. e.g., Composition 1, e.g., 1.1-1.39, comprise 5 to 70 weight % of an abrasive, e.g., 6 to 60 weight % of an abrasive, e.g., 7 to 50 weight percent of an abrasive, e.g., 8 to 40% of an abrasive, e.g., 9 to 30% of an abrasive, e.g., 10 to 30% of an abrasive, e.g., 10 to 20% of an abrasive.

Abrasives that may be used in the oral care compositions disclosed herein, e.g., Composition 1, e.g., 1.1-1.39, include, for example, a calcium phosphate abrasive, e.g., tricalcium phosphate ($Ca_3(PO_4)_2$), hydroxyapatite ($Ca_{10}(PO_4)_6(OH)_2$), dicalcium phosphate dihydrate ($CaHPO_4.2H_2O$, also sometimes referred to herein as DiCal), calcium pyrophosphate, and mixtures thereof. Calcium carbonate, e.g., precipitated calcium carbonate, may also be employed as an abrasive.

Other abrasives that may be used in the oral care compositions disclosed herein, e.g., Composition 1, e.g., 1.1-1.39, include, for example, silica abrasives such as precipitated silicas having a mean particle size of up to about 20 microns, such as Zeodent 115®, marketed by J. M. Huber, as well as sodium metaphosphate, potassium metaphosphate, aluminum silicate, calcined alumina, bentonite or other siliceous materials, or mixtures thereof. Silica abrasives used herein, as well as the other abrasives, may have an average particle size ranging between about 0.1 and about 30 microns, e.g., between about 5 and about 15 microns. The silica abrasives may be from precipitated silica or silica gels, such as the silica xerogels described in U.S. Pat. No. 3,538,230 to Pader et al. and U.S. Pat. No. 3,862,307 to Digiulio, incorporated herein by reference in their entirety. Particular silica xerogels are marketed under the trade name Syloid® by the W. R. Grace & Co. Davison Chemical Division. Precipitated silica materials include those marketed by the J. M. Huber Corp. under the trade name Zeodent®, including the silica carrying the designation Zeodent 115 and 119. Those silica abrasives are described in U.S. Pat. No. 4,340,583 to Wason, incorporated herein by reference in its entirety.

In some embodiments, abrasives that may be used in the oral care compositions disclosed herein, e.g., Composition 1, e.g., 1.1-1.39, include silica gels and precipitated amorphous silica having an oil absorption value of about less than about 100 cc/100 g silica and in the range of about 45 cc/100 g to about 70 cc/100 g silica. Oil absorption values are measured using the ASTA Rub-Out Method D281. In some embodiments, the silica comprises colloidal particles having an average particle size of about 3 microns to about 12 microns, and about 5 to about 10 microns.

In some embodiments, the abrasive comprises a large fraction of very small particles, e.g., having a d50 less than about 5 microns, e.g., small particle silica (SPS) having a d50 of about 3 to about 4 microns, e.g., Sorbosil AC43® (Ineos). Such small particles may be used in formulations targeted at reducing hypersensitivity. The small particle component may be present in combination with a second larger particle abrasive.

Low oil absorption silica abrasives that may be used in the oral care compositions disclosed herein, e.g., Composition 1, e.g., 1.1-1.39, are marketed under the trade designation Sylodent WXA® by Davison Chemical Division of W.R. Grace & Co., Baltimore, Md. 21203. Sylodent 650 XWA®, a silica hydrogel composed of particles of colloidal silica having a water content of about 29% by weight averaging about 7 to about 10 microns in diameter, and an oil absorption of less than about 70 cc/100 g of silica is an example of a low oil absorption silica abrasive that may be used in the oral care compositions disclosed herein, e.g., Composition 1, e.g., 1.1-1.39.

In some embodiments, the oral care composition disclosed herein, e.g., Composition 1, e,g, 1.1-1.39, comprise a high cleaning silica.

In some embodiments, the oral care compositions disclosed herein, e.g., Composition 1, e.g., 1.1-1.39, comprise a sweetener. In some embodiments, the oral care compositions disclosed herein, e.g., Composition 1, e.g., 1.1-1.39, comprise 0.005 to 10 weight % of a sweetener, e.g., 0.01 to 10 weight % of a sweetener, e.g., 0.1 to 10 weight % of a sweetener, e.g., from 0.1 to 5 weight % of a sweetener, e.g., from 0.1 to 3 weight % of a sweetener, e.g., from 0.1 to 1 weight % of a sweetener. e.g., from 0.1 to 0.5 weight % of a sweetener. Sweeteners that may be used in the oral care compositions disclosed herein, e.g., Composition 1, e.g., 1.1-1.39, include, for example, sucrose, glucose, saccharin, sucralose, dextrose, levulose, lactose, mannitol, sorbitol, fructose, maltose, xylitol, saccharin salts (e.g., sodium saccharin), thaumatin, aspartame, D-tryptophan, dihydrochalcones, acesulfame, cyclamate salts, and mixtures thereof. In some embodiments, sodium saccharin is used as the sweetener in the oral care compositions disclosed herein, e.g., Composition 1, e.g., 1.1-1.39. In some embodiments, the oral care compositions disclosed herein, e.g., Composition 1. e.g., 1.1-1.39, comprise 0.005 to 10 weight % sodium saccharin, e.g., 0.01 to 10 weight % sodium saccharin, e.g., 0.1 to 10 weight % sodium saccharin, e.g., from 0.1 to 5 weight % sodium saccharin, e.g., from 0.1 to 3 weight % sodium saccharin, e.g., from 0.1 to 1 weight % sodium saccharin, e.g., from 0.1 to 0.5 weight % sodium saccharin.

In some embodiments, the oral care compositions disclosed herein, e.g., Composition 1, e.g., 1.1-1.39, comprise a flavorant. In some embodiments, the oral care compositions disclosed herein, e.g., Composition 1. e.g., 1.1-1.39, comprise 0.1 to 5 weight % of a flavorant, e.g., 0.2 to 4 weight % of a flavorant, e.g., 0.3 to 3 weight % of a flavorant, e.g., 0.4 to 2 weight % of a flavorant, e.g., 0.5 to 2 weight % of a flavorant, e.g., 0.6 to 2 weight % of a flavorant. e.g., 0.7 to 2 weight % of a flavorant, e.g., 0.8 to 2 weight % of a flavorant e.g., 0.9 to 2 weight % of a flavorant, e.g., 1 to 2 weight % of a flavorant. Flavorants that may be used in the oral care compositions disclosed herein, e.g., Composition 1, e.g., 1.1-1.39, include, for example, essential oils, as well as various flavoring aldehydes, esters, alcohols, and similar materials, as well as menthol, carvone, and anethole, as well as mixtures thereof. Examples of essential oils include oils of spearmint, peppermint, wintergreen, sassafras, clove, sage, eucalyptus, marjoram, cinnamon, lemon, lime, grapefruit, and orange. In some embodiments, a mixture of peppermint oil and spearmint oil is used as the flavorant in the oral care compositions disclosed herein, e.g., Composition 1. e.g., 1.1-1.39.

In some embodiments, the oral care compositions disclosed herein, e.g., Composition 1, e.g., 1.1-1.39, comprise a visual aid, including but not limited to a pigment, a dye, speckles, beads, strips, and mixtures thereof. In some embodiments, the oral care compositions disclosed herein, e.g., Composition 1, e.g., 1.1-1.39, comprise 0.001 to 20 weight % of a visual aid, e.g., 0.01 to 10 weight % of a visual aid, e.g., 0.1 to 10 weight % of a visual aid, e.g., 0.1 to 5 weight % of a visual aid, e.g., 0.1 to 3 weight % of a visual aid, e.g., 0.1 to 1 weight % of a visual aid, e.g., 0.2 to 0.9 weight % of a visual aid, e.g., 0.3 to 0.8 weight % of a visual aid, e.g., 0.5 to 0.8 weight % of a visual aid. In some embodiments, the oral care compositions disclosed herein, e.g., Composition 1, e.g., 1.1-1.39, comprise titanium dioxide. In some embodiments, the oral care compositions disclosed herein, e.g., Composition 1, e.g., 1.1-1.39, comprise 0.001 to 20 weight % of titanium dioxide, e.g., 0.01 to 10 weight % titanium dioxide, e.g., 0.1 to 10 weight % o titanium dioxide, e.g., 0.1 to 5 weight % titanium dioxide, e.g., 0.1 to 3 weight % titanium dioxide, e.g., 0.1 to 1 weight % titanium dioxide, e.g., 0.2 to 0.9 weight % titanium dioxide. e.g., 0.3 to 0.8 weight % titanium dioxide, e.g., 0.5 to 0.8 weight % titanium dioxide.

In some embodiments, the oral care compositions disclosed herein, e.g., Composition 1, e.g., 1.1-1.39, further comprise an anti-caries agent. In some embodiments, the oral care compositions disclosed herein, e.g., Composition 1. e.g., 1.1-1.39, comprise 0.005 to 10 weight % of the anti-caries agent, e.g., 0.01 to 10 weight % of the anti-caries agent, e.g., 0.01 to 5 weight % of the anti-caries agent, e.g., 0.01 to 1 weight % of the anti-caries agent, e.g., 0.01 to 0.3 weight % of the anti-caries agent, e.g., 0.1 to 5 weight % of the anti-caries agent, e.g., 0.1 to 2 weight % of the anti-caries agent, e.g., 0.1 to 1 weight % of the anti-caries agent, e.g., 0.1 to 0.8 weight % of the anti-caries agent, e.g., 0.1 to 0.6 weight % of the anti-caries agent, e.g., 0.1 to 0.5 weight % of the anti-caries agent, e.g., 0.1 to 0.3 weight % of the anti-caries agent. In some embodiments, the anti-caries agent is a fluoride ion source. In some embodiments, the oral care compositions disclosed herein, e.g., Composition 1, e.g., 1.1-1.39, further comprise 0.005 to 10 weight % of the anti-caries agent which is a fluoride ion source, e.g., 0.01 to 10 weight % of the anti-caries agent which is a fluoride ion source, e.g., 0.01 to 5 weight % of the anti-caries agent which is a fluoride ion source, e.g., 0.01 to 1 weight % of the anti-caries agent which is a fluoride ion source, e.g., 0.01 to 0.3 weight % of the anti-caries agent which is a fluoride ion source, e.g., 0.1 to 5 weight % of the anti-caries agent which is a fluoride ion source, e.g., 0.1 to 2 weight % of the anti-caries agent which is a fluoride ion source, e.g., 0.1 to 1 weight % of the anti-caries agent which is a fluoride ion source, e.g., 0.1 to 0.8 weight % of the anti-caries agent which is a fluoride ion source, e.g., 0.1 to 0.5 weight % of the anti-caries agent which is a fluoride ion source, e.g., 0.1 to 0.4 weight % of the anti-caries agent which is a fluoride ion source, e.g., 0.1 to 0.3 weight % of the anti-caries agent which is a fluoride ion source. Examples of fluoride ion sources that may be used in the oral compositions disclosed herein, e.g., Composition 1, e.g., 1.1-1.39, are found in U.S. Pat. No. 3,535,421 to Briner et al.; U.S. Pat. No. 4,885,155 to Parran, Jr. et al., and U.S. Pat. No. 3,678,154 to Widder et al, incorporated herein by reference in their entirety. Other examples of fluoride ion sources include, for example, stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof. In certain embodiments the fluoride ion source includes stannous fluoride, sodium fluoride, and sodium monofluorophosphate, as well as mixtures thereof. In some embodiments, the anti-caries agent is sodium fluoride. In some embodiments, the oral care compositions disclosed herein, e.g., Composition 1, e.g., 1.1-1.39, comprise 00.005 to 10 weight % sodium fluoride, e.g., 0.01 to 10 weight % sodium fluoride, e.g., 0.01 to 5 weight % sodium fluoride, e.g., 0.01 to 1 weight % sodium fluoride, e.g., 0.01 to 0.3 weight % sodium fluoride, e.g., 0.1 to 5 weight % sodium fluoride, e.g., 0.1 to 2 weight % sodium fluoride, e.g., 0.1 to 1 weight % sodium fluoride, e.g., 0.1 to 0.8 weight % sodium fluoride, e.g., 0.1 to 0.5 weight % sodium fluoride, e.g., 0.1 to 0.4 weight % sodium fluoride, e.g., 0.1 to 0.3 weight % sodium fluoride.

In some embodiments, the oral care compositions disclosed herein, e.g., Composition 1, e.g., 1.1-1.39, comprise the anti-caries agent which is a fluoride ion source in an amount sufficient to supply 25 ppm to 25,000 ppm of fluoride ions, e.g., from 100 to 20,000 ppm of fluoride ions, e.g., from 300 to 15,000 ppm of fluoride ions, e.g., from 500 to 10,000 ppm of fluoride ions. e.g., from 500 to 8.000 ppm of fluoride ions, e.g., from 500 to 6,000 ppm of fluoride ions, e.g., from 500 to 4.000 ppm of fluoride ions, e.g., from 500 to 2,000 ppm of fluoride ions. e.g., from 500 to 1.800 ppm of fluoride ions, e.g., from 1000 to 1600 ppm, e.g., 1450 ppm of fluoride ions. The appropriate level of fluoride ions will depend on the particular application. In some embodiments, a toothpaste for consumer use comprises the anti-caries agent which is a fluoride ion source in an amount sufficient to supply from 1.000 to 1,500 ppm of fluoride ions, with pediatric toothpaste having somewhat less. In some embodiments, a dentifrice or coating for professional application comprises the anti-caries agent which is a fluoride ion source in an amount sufficient to supply from 5,000 to 25.000 ppm of fluoride ions.

In some embodiments, the oral care compositions disclosed herein, e.g., Composition 1, e.g., 1.1-1.39, comprise an anti-bacterial agent or an anti-attachment agent. In some embodiments, the oral care compositions disclosed herein, e.g., Composition 1, e.g., 1.1-1.39, comprise 0.01 to 10 weight % of an anti-bacterial agent, e.g., 0.1 to 10 weight % of an anti-bacterial agent, e.g., 0.5 to 5 weight % of an anti-bacterial agent, e.g., 0.01 to 5 weight % of an anti-bacterial agent, e.g., 0.03 to 4 weight % of an anti-bacterial agent, e.g., 0.05 to 3 weight % of an anti-bacterial agent, e.g., 0.07 to 2 weight % of an anti-bacterial agent. e.g., 0.09 to 1 weight %, of an anti-bacterial agent, e.g., 0.1 to 0.9 weight %, of an anti-bacterial agent, e.g., 0.1 to 0.8 weight % of an anti-bacterial agent, e.g., 0.1 to 0.7 weight % of an anti-bacterial agent, e.g., 0.1 to 0.6 weight % of an anti-bacterial agent. e.g., 0.1 to 0.5 weight % of an anti-bacterial agent, e.g., 0.1 to 0.4 weight % of an anti-bacterial agent, e.g., 0.2 to 0.4 weight % of an anti-bacterial agent. The amount of the anti-bacterial agent will vary depending on the type of oral care composition, with levels used in toothpaste being, for example, 5 to 15 times greater than used in mouthwash. For example, a mouthwash comprising triclosan may comprise, e.g., 0.03 weight % triclosan while a toothpaste comprising triclosan toothpaste may comprise 0.3 weight % triclosan. Examples of fluoride ion sources that may be used in the oral compositions disclosed herein, e.g., Composition 1, e.g., 1.1-1.39, include, for example, halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol salifluor, metal ions (e.g., zinc salts, for example, zinc citrate, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts, methyl hydroxybenzoate, and mixtures thereof.

A whitening agent whitens a tooth to which it is applied. In some embodiments, the oral care compositions disclosed herein, e.g., Composition 1, e.g., 1.1-1.39, comprise a whitening agent. In some embodiments, the oral care compositions disclosed herein, e.g., Composition 1, e.g., 1.1-1.39, comprise a whitening agent in a dental surface-whitening effective amount, e.g., 0.1 to 90 weight % whitening agent, e.g., 0.5 to 50 weight % whitening agent, e.g., 1 to 30 weight % whitening agent, e.g., 2 to 10 weight % whitening agent. Examples of whitening agents that may be used in the oral compositions disclosed herein, e.g., Composition 1, e.g., 1.1-1.39, include, for example, peroxides, metal chlorites, perborates, percarbonates, peroxyacids, hypochlorites, and mixtures thereof. In some embodiments, the whitening agent is hydrogen peroxide or a hydrogen peroxide source, for example, urea peroxide or a peroxide salt or complex (for example, peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or a hydrogen peroxide polymer complex (for example, a peroxide-polyvinyl pyrrolidone polymer complex).

Any of the preceding oral care compositions, wherein the composition is a mouthwash, toothpaste, tooth gel, tooth powder, non-abrasive gel, mousse, foam, mouth spray, lozenge, oral tablet, dental implement, or pet care product.

Any of the preceding oral care compositions, wherein the composition is a mouthwash.

Any of the preceding oral care compositions, wherein the composition is a toothpaste.

Further provided is a method (Method A) for the treatment and/or inhibition of a chemical stain, plaque, and/or tartar on a dental surface, comprising contacting the dental surface with any of the preceding oral care compositions.

Further provided herein is Method A as follows:
A.1 Method A wherein the composition is Composition 1, e.g., 1.1-1.39.
A.2 Method A or A.1 wherein the method is for the treatment of a chemical stain, plaque, acid erosion, and/or tartar on the dental surface.
A.3 Method A.2 wherein the method is for the treatment of a chemical stain on the dental surface.
A.4 Method A.2 wherein the method is for the treatment of plaque on the dental surface.
A.5 Method A.2 wherein the method is for the treatment of acid erosion on the dental surface.
A.6 Method A.2 wherein the method is for the treatment of tartar on the dental surface.
A.7 Method A or A.1 wherein the method is for the inhibition of a chemical stain, plaque, and/or tartar on the dental surface.
A.8 Method A.7 wherein the method is for the inhibition of a chemical stain on the dental surface.
A.9 Method A.7 wherein the method is for the inhibition of plaque on the dental surface.
A.10 Method A.7 wherein the method is for the inhibition of acid erosion on the dental surface.
A.11 Method A.7 wherein the method is for the inhibition of tartar on the dental surface.
A.12 Method A or A.1-A.11 wherein the dental surface is a human tooth.
A.13 Method A or A.1-A.12 wherein the composition is contacted with the dental surface by brushing.

Further provided is a method (Method B) for the treatment and/or inhibition of gum disease comprising contacting the oral cavity with any of the preceding oral care compositions.

Further provided herein is Method B as follows:
B.1 Method B wherein the composition is Composition 1, e.g., 1.1-1.39.
B.2 Method B or B.1 wherein the method is for the treatment of gum disease.
B.3 Method B, B.1, or B.2 wherein the gum disease is gingivitis.
B.4 Method B, B.1, or B wherein the gum disease is periodontitis.
B.5 Method B or B.1 wherein the method is for the inhibition of gum disease.
B.6 Method B, B.1, or B.5 wherein the gum disease is gingivitis.
B.7 Method B, B.1, or B.5 wherein the gum disease is periodontitis.
B.8 Method B or B.1-B.7 wherein the oral cavity is a human oral cavity.
B.9 Method B or B.1-B.8 wherein the composition is contacted with the oral cavity by brushing.

Further provided is a method (Method C) for the treatment and/or inhibition of halitosis comprising contacting the oral cavity with any of the preceding oral care compositions.

Further provided herein is Method C as follows:
C.1 Method C wherein the composition is Composition 1, e.g., 1.1-1.39.
C.2 Method C or C.1 wherein the oral cavity is a human oral cavity.
C.3 Method C, C.1, or C.2 wherein the composition is contacted with the oral cavity by brushing.

Further provided is a method (Method D) for inhibiting biofilm formation on a dental surface comprising contacting the dental surface with any of the preceding oral care compositions.

Further provided herein is Method D as follows:
D.1 Method D wherein the composition is Composition 1, e.g., 1.1-1.39.
D.2 Method D or D.1 wherein the dental surface is a human tooth.
D.3 Method D. D.1, or D.2 wherein the composition is contacted with the dental surface by brushing.

Further provided is a method (Method E) for treating and/or inhibiting bacteria from sticking together and growing into bigger colonies in an oral cavity comprising contacting the oral cavity with any of the preceding oral care compositions.

Further provided herein is Method E as follows:
E.1 Method E wherein the composition is Composition 1, e.g., 1.1-1.39.
E.2 Method E or E.1 wherein the oral cavity is a human oral cavity.
E.3 Method E, E.1, or E.2 wherein the composition is contacted with the oral cavity by brushing.

Further provided is a use (Use A) of any of the preceding oral care compositions for the treatment and/or inhibition of a chemical stain, plaque, and/or tartar on a dental surface.

Further provided herein is Use A as follows:
A.1 Use A wherein the composition is Composition 1, e.g., 1.1-1.39.
A.2 Use A or A.1 wherein the use is for the treatment of a chemical stain, plaque, acid erosion, and/or tartar on the dental surface.
A.3 Use A.2 wherein the use is for the treatment of a chemical stain on the dental surface.
A.4 Use A.2 wherein the use is for the treatment of plaque on the dental surface.
A.5 Use A2 wherein the use is for the treatment of acid erosion on the dental surface.
A.6 Use A.2 wherein the use is for the treatment of tartar on the dental surface.
A.7 Use A or A.1 wherein the use is for the inhibition of a chemical stain, plaque, acid erosion, and/or tartar on the dental surface.
A.8 Use A.7 wherein the use is for the inhibition of a chemical stain on the dental surface.
A.9 Use A.7 wherein the use is for the inhibition of plaque on the dental surface.
A.10 Use A.7 wherein the use is for the inhibition of acid erosion on the dental surface.
A.11 Use A.7 wherein the use is for the inhibition of tartar on the dental surface.
A.12 Use A or A.1-A.11 wherein the dental surface is a human tooth.
A.13 Use A or A.1-A.12 wherein the composition is contacted with the dental surface by brushing.

Further provided is a use (Use B) of any of the preceding oral care compositions for the treatment and/or inhibition of gum disease in an oral cavity.

Further provided herein is Use B as follows:
B.1 Use B wherein the composition is Composition 1, e.g., 1.1-1.39.
B.2 Use B or B.1 wherein the use is for the treatment of gum disease.
B.3 Use B, B.1, or B.2 wherein the gum disease is gingivitis.
B.4 Use B, B.1, or B wherein the gum disease is periodontitis.
B.5 Use B or B.1 wherein the use is for the inhibition of gum disease.
B.6 Use B, B.1, or B.5 wherein the gum disease is gingivitis.

B.7 Use B, B.1, or B.5 wherein the gum disease is periodontitis.

B.8 Use B or B.1-B.7 wherein the oral cavity is a human oral cavity.

B.9 Use B or B.1-B.8 wherein the composition is contacted with the oral cavity by brushing.

Further provided is a use (Use C) of any of the preceding oral care compositions for the treatment and/or inhibition of halitosis in an oral cavity.

Further provided herein is Use C as follows:

C.1 Use C wherein the composition is Composition 1, e.g., 1.1-1.39.

C.2 Use C or C.1 wherein the oral cavity is a human oral cavity.

C.3 Use C, C.1, or C.2 wherein the composition is contacted with the oral cavity by brushing.

Further provided is a use (Use D) of any of the preceding oral care compositions for the inhibition of biofilm formation on a dental surface.

Further provided herein is Use D as follows:

D.1 Use D wherein the composition is Composition 1, e.g., 1.1-1.39.

D.2 Use D or D.1 wherein the oral cavity is a human oral cavity.

D.3 Use D, D.1, or D.2 wherein the composition is contacted with the oral cavity by brushing.

Further provided is a use (Use E) of any of the preceding oral care compositions for treating and/or inhibiting bacteria from sticking together and growing into bigger colonies in an oral cavity.

Further provided herein is Use E as follows:

E.1 Use E wherein the composition is Composition 1, e.g., 1.1-1.39.

E.2 Use E or E.1 wherein the oral cavity is a human oral cavity.

E.3 Use E, E.1, or E.2 wherein the composition is contacted with the oral cavity by brushing.

As used herein, "inhibition" refers to reduction of stains that would otherwise form or develop subsequent to the time of the treatment. Such inhibition can range from a small but observable or measurable reduction to complete inhibition of subsequent staining, by comparison with an untreated or placebo-treated dental surface.

Where the dental surface is substantially free of chemical stains, Method A, e.g., A.1-A.10, and Use B, e.g., B.1-B.10, are effective to inhibit formation and development of new chemical stains, as can occur for example by oral use of tobacco products (including smoking) or by drinking tea, coffee, coke, or red wine subsequent to treatment according to the method. Where the dental surface already possesses some degree of chemical staining, Method A, e.g., A.1-A.10, and Use B, e.g., B.1-B.10, are effective to inhibit further development of the existing stain. In some embodiments, the Method A, e.g., A.1-A.10, and Use B, e.g., B.1-B.10, can remove, partially or completely, an existing chemical stain as well as inhibit subsequent staining.

EXAMPLES

Example 1

A toothpaste containing 0.7% stannous chloride ($SnCl_2$) is dosed with phosphate/acrylate co-polymer (0.4% active ingredient) polymer and its in vitro stain prevention efficacy is compared to that of the stannous toothpaste without the co-polymer and to a water control. In general, the stain prevention efficacy is quantified using a chromameter to obtain the L (lightness) value, which measures the light reflected off the surface of a hydroxyapatite (HAP) disc following treatment of the disc with a 1:2 dentifrice:water slurry and three cycles of treatment with coffee and saliva. Specifically, HAP discs are soaked in saliva overnight at 37° C. and then treated with a 1:2 dentifrice:water slurry for 5 min. The initial L value is then measured. Next, the discs are exposed to coffee for 15 min., rinsed with distilled, deionized water, and incubated at 37° C. for 20 min. The staining process is repeated for a total of three times and the final L value is obtained. The change in lightness indicated the efficacy of the dentifrice at preventing coffee stains. The results are shown in Table 2. The addition of the polymer is able to significantly (p<0.05) reduce the staining potential of the stannous-containing toothpaste by coating the surface of the HAP disc and preventing the stain from adhering.

TABLE 2

| Product | ΔL |
| --- | --- |
| 0.7% $SnCl_2$ Toothpaste | −14.98 |
| 0.7% $SnCl_2$ Toothpaste with 0.4% phosphate acrylate co-polymer | −10.1 |
| Water Control | −16.48 |

What is claimed is:

1. An oral care composition comprising a phosphate/acrylate co-polymer, a tin salt, and an orally acceptable carrier, wherein the phosphate/acrylate co-polymer is a co-polymerized product of a mixture of acrylic acid, methacrylic acid, and a mixture of 2-hydroxyethyl methacrylate phosphates of Formula 1:

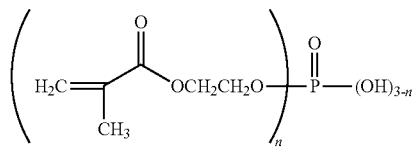

wherein n is 0, 1 or 2.

2. The composition of claim 1, wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 70-90%; methacrylic acid in a molar percentage of 5-20%, and hydroxyethyl methacrylate phosphates of Formula 1 in a molar percentage of 1-10%.

3. The composition of claim 1, wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 80-90% or 85%; methacrylic acid in a molar percentage of 5-15% or 11%, and hydroxyethyl methacrylate phosphates of Formula 1 in a molar percentage of 2-6% or 4%.

4. The composition of claim 1, wherein the phosphate/acrylate copolymer is a random copolymer having a weight average molecular weight of 10,000 to 500,000, and the phosphate/acrylate copolymer is below its glass transition temperature.

5. The composition of claim 4, wherein the weight average molecular weight is 10,000 to 200,000 grams per mole, optionally, 10,000 to 40,000, 15,000 to 25,000, or 17,000 to 23,000 grams per mole.

6. The composition of claim 1 wherein the tin salt is selected from stannous chloride, stannous fluoride and mixtures thereof.

7. The composition of claim 1, wherein the tin salt comprises $SnCl_2$.

8. The composition of claim 1, wherein the composition comprises 0.1 to 10 weight % $SnCl_2$, optionally 0.1 to 5 weight %, 0.1 to 3 weight %, 0.1 to 1.5 weight %, or 0.5 to 1.2 weight % $SnCl_2$.

9. The composition of claim 1, wherein the composition comprises one or more of water, a thickener, a buffer, a humectant, a surfactant, an abrasive, a sweetener, a flavorant, a pigment, a dye, an anti-caries agent, an anti-bacterial, a whitening agent, a desensitizing agent, a vitamin, a preservative, an enzyme, or a mixture thereof.

10. The composition of claim 9, wherein the anti-bacterial agent is selected from the group consisting of triclosan, cetylpyridinium chloride (CPC), chlorhexidine (CHX), water soluble zinc salts, water insoluble zinc salts, zinc oxide, zinc citrate, or a mixture thereof.

11. The composition of claim 1, wherein the composition is a mouthwash, toothpaste, tooth gel, tooth powder, non-abrasive gel, mousse, foam, mouth spray, lozenge, oral tablet, dental implement, or pet care product.

12. A method for the treatment and/or inhibition of a chemical stain, plaque, acid erosion, and/or tartar on a dental surface, comprising contacting the dental surface with a composition of claim 1.

13. A method for the treatment and/or inhibition of gum disease comprising contacting the oral cavity with a composition of claim 1.

14. A method for the treatment and/or inhibition of halitosis comprising contacting the oral cavity with a composition of claim 1.

15. A method for the inhibition of biofilm formation on a dental surface comprising contacting the oral cavity with a composition of claim 1.

16. A method for treating and/or inhibiting bacteria from sticking together and growing into bigger colonies in an oral cavity comprising contacting the oral cavity with a composition of claim 1.

* * * * *